(12) United States Patent
Sundstrom

(10) Patent No.: US 8,617,832 B2
(45) Date of Patent: Dec. 31, 2013

(54) **METHOD FOR IDENTIFYING AN AGENT THAT INHIBITS *CANDIDA ALBICANS*—MEDIATED HOST CELL DIFFERENTIATION**

(75) Inventor: Paula Sundstrom, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 27 days.

(21) Appl. No.: 13/391,722

(22) PCT Filed: Aug. 13, 2010

(86) PCT No.: PCT/US2010/045476
§ 371 (c)(1),
(2), (4) Date: Feb. 22, 2012

(87) PCT Pub. No.: WO2011/025677
PCT Pub. Date: Mar. 3, 2011

(65) Prior Publication Data
US 2012/0156697 A1     Jun. 21, 2012

Related U.S. Application Data

(60) Provisional application No. 61/236,917, filed on Aug. 26, 2009.

(51) Int. Cl.
*G01N 33/53* (2006.01)
(52) U.S. Cl.
USPC ............. 435/7.31; 435/29; 435/7.2; 435/4; 435/255.4

(58) Field of Classification Search
None
See application file for complete search history.

(56) References Cited

U.S. PATENT DOCUMENTS

2007/0237747 A1   10/2007   Angel et al. ............... 424/93.7
2007/0276049 A1   11/2007   Schlievert et al. ........... 514/738

OTHER PUBLICATIONS

Harrison et al (Applied and Environ. Microbiol. Published ahead of print Jun. 2007. Print Aug. 2007. 73(15): 4940-4949).*
Ollert et al (Infection and Immunity. Nov. 1993. 61(11): 4560-4568.*
D'Souza et al. "$Ca^{2+}$ and BMP-6 Signaling Regulate E2F Epidermal Keratinocyte Differentiation" The Journal of Biological Chemistry 2001 vol. 276(26):23531-23538.
Filler et al. "Penetration and Damage of Endothelial Cells by *Candida albicans*" Infection and Immunity 1995 vol. 63(3):976-983.
Kolotila, M.P. and Diamond, R.D. "Stimulation of Neutrophil Actin Polymerization and Degranulation by Opsonized and Unopsonized *Candida albicans* Hyphae and Zymosan" Infection and Immunity 1988 vol. 56(8):2016-2022.
Park et al. "Role of the Fungal Ras-protein Kinase A Pathway in Governing Epithelial Cell Interactions During Oropharyngeal Candidiasis" Cellular Microbiology 2005 vol. 7(4):499-510.
Ponniah et al. "State of Differentiation Defines Buccal Epithelial Cell Affinity for Cross-linking to *Candida albicans* Hwp1" Journal of Oral Pathology and Medicine 2007 vol. 36(8):456-467.
Rollenhagen et al. "Stimulation of Cell Motility and Expression of Late Markers of Differentiation in Human Oral Keratinocytes by *Candida albicans*" Cellular Microbiology 2009 vol. 11(6):946-966.
Sandovsky-Losica et al. "Effect of *Candida albicans* Metabolite(s) on Cellular Actin" FEMS Microbiology Letters 2002 vol. 215:57-62.
Schaller et al. "Hydrolytic Enzymes as Virulence Factors of *Candida albicans*" Mycoses 2005 vol. 48(6):365-377.
Schindler, B. and Segal, E. "*Candida albicans* Metabolite Affect the Cytoskeleton and Phagocytic Activity of Murine Macrophages" Medical Mycology 2008 vol. 46:251-258.
Tsarfaty et al. "Cellular Actin is Affected by Interaction with *Candida albicans*" FEMS Microbiology Letters 2000 vol. 189:225-232.
Weindl et al. "Human Epithelial Cells Establish Direct Antifungal Defense Through TLR4-Mediated Signaling" The Journal of Clinical Investigation 2007 vol. 117(12):3664-3672.
Wozniok et al. "Induction of ERK-Kinase Signalling Triggers Morphotype-Specific Killing of *Candida albicans* Filaments by Human Neutrophils" Cellular Microbiology 2008 vol. 10(3):807-820.
Villar et al. "Invasive Phenotype of *Candida albicans* Affects the Host Proinflammatory Response to Infection" Infection and Immunity 2005 vol. 73(8):4588-4595.

* cited by examiner

*Primary Examiner* — Jennifer Graser
(74) *Attorney, Agent, or Firm* — Licata & Tyrrell, P.C.

(57) ABSTRACT

The present invention features a method for identifying an agent that inhibits *Candida albicans*-mediated differentiation of keratinocytes. Agents identified by the screening assay of the invention find application in the prevention and treatment of candidiasis.

2 Claims, No Drawings

METHOD FOR IDENTIFYING AN AGENT THAT INHIBITS *CANDIDA ALBICANS*—MEDIATED HOST CELL DIFFERENTIATION

This application is a U.S. National Stage Application of PCT/US2010/045476 filed Aug. 13, 2010 and claims benefit of priority to U.S. Provisional Application Ser. No. 61/236,917, filed Aug. 26, 2009, the contents of each of which are incorporated herein by reference in their entirety.

This invention was made with government support under contract number DE011375 awarded by the National Institutes of Health. The government has certain rights in the invention.

INTRODUCTION

Background of the Invention

The stratified squamous epithelium of wet mucosal surfaces of immunocompromised mammalian hosts may become heavily invaded by the opportunistic fungal pathogen, *Candida albicans*. The greatest fungal burdens are associated with antibiotics, the presence of HIV, leukemia, malignancy, radiation therapy for head and neck cancer or other risk factors that interfere with immunocompetence (Farah, et al. (2000) *Clin. Dermatol.* 18:553-562; Clarkson, et al. (2004) *Cochrane Database Syst. Rev.* CD001972; Fidel (2006) *Adv. Dent. Res.* 19:80-84; Soysa, et al. (2008) *Oral Dis.* 14:138-143). Heavy gastrointestinal colonization is an important risk factor for invasive candidiasis in cancer patients and in very low-birth-weight neonates (Huang, et al. (1998) *Pediatr. Infect. Dis. J.* 17:819-822; El-Masry, et al. (2002) *Acta Paediatr.* 91:198-202; Sims, et al. (2005) *Arch. Med. Res.* 36:660-671). Understanding the molecular mechanisms that lead to invasion of the oral epithelium is important for developing strategies to interfere with mucosal candidiasis and its potential long-term complications.

A hallmark of pseudomembranous candidiasis or thrush is the presence of hyperkeratinization, which is an increased amount of keratinized squames on the surface of the epithelium (Neville, et al. (2002) Fungal and protozoal diseases. In: *Oral and Maxillofacial Pathology*. Philadelphia:W.B. Saunders Company, pp. 189-197). Hyperkeratinization is a general keratinocyte response to impairment in the permeability barrier of the epithelium (Ajani, et al. (2007) *Exp. Cell. Res.* 313:3005-3015). In the specific case of candidiasis, the hyperkeratinized region provides an environment that supports heavy growth of *C. albicans*, which does not penetrate the intermediate stratum spinosum and basal keratinocyte layers (Eversole, et al. (1993) *J. Oral Pathol. Med.* 22:303-307; Eversole, et al. (1997) *Oral Surg. Oral Med. Oral Pathol. Oral Radiol. Endod.* 84:372-380; Neville, et al. (2002) supra; Sundstrom, et al. (2002a) *J. Infect. Dis.* 185:521-530; Sundstrom (2006) Candida albicans hypha formation and virulence. In Heitman, J. (ed.). *Molecular Principles of Fungal Pathogenesis*. Washington D.C.:American Society for Microbiology Press, pp. 45-47). The ability of *C. albicans* to proliferate in mucosal tissues may be dependent on hyperkeratosis for generating a region of the mucosa that is not inhibitory to fungal growth; for example, the antimicrobial protein, calprotectin (Brandtzaeg, et al. (1995) *Adv. Exp. Med. Biol.* 371A:201-206), which is distributed beneath the keratinized layers in the stratum spinosum, is associated with intermediate stages of differentiation (Eversole, et al. (1992) *Arch. Oral Biol.* 37:963-968). Thus, the extent of differentiation appears to be of key importance in tipping the balance between susceptibility and resistance of keratinocytes to invading fungi.

Studying *C. albicans* epithelial interactions is complicated by the multicellularity of the epithelium that is composed primarily of keratinocytes in progressive states of differentiation from the basal to the surface layers. It has been suggested that the differentiation status of the epithelium may contribute to the pathogenesis of candidiasis. Binding of the *C. albicans* adhesin Hwp1p to buccal keratinocytes is correlated with the presence of the late-stage markers SPRR3 and keratin 13 and not with an early-stage marker, involucrin (Ponniah, et al. (2007) *J. Oral Pathol. Med.* 36:456-467). Less mature keratinocytes show minimal binding to Hwp1 in in vitro assays (Ponniah, et al. (2007) supra).

Several processes that contribute to the virulence of *C. albicans* have been described, including adhesion, morphological and phenotypic switching, and the production of secreted hydrolytic enzymes (Schaller, et al. (2005) *Mycoses* 48:365-377). The importance of the Ras-cAMP signaling pathway and the interconversion between yeast, pseudohyphal and hyphal growth forms in virulence has been demonstrated using *C. albicans* mutants that are deficient in morphogenesis (Park, et al. (2005) *Cell. Microbiol.* 7:499-510). Hyphal growth forms are important for adherence and invasion (Kumamoto & Vinces (2005) *Cell. Microbiol.* 7:1546-1554; Kumamoto & Vinces (2005) *Annu. Rev. Microbiol.* 59:113-133). The hypha-specific adhesins Hwp1 and Als3 have been shown to play important roles in oreosophageal candidiasis and invasion of the RHE, respectively. Als3 has also been shown to facilitate endocytosis through interactions between hyphae and E-cadherin (Phan, et al. (2007) *PLoS Biol.* 5:e64). Hypha-specific aspartyl proteinases have also been shown to play important roles in virulence of candidiasis (Sanglard, et al. (1997) supra; Kretschmar, et al. (1999) *Infect. Immun.* 67:6637-6642; Felk, et al. (2002) *Infect. Immun.* 70:3689-3700; Naglik, et al. (2003) *Microbiol. Mol. Biol. Rev.* 67:400-428; Jackson, et al. (2007) *Invest. Ophthalmol. Vis. Sci.* 48:3559-3565).

It has been shown that keratinocytes produce pro-inflammatory cytokines in response to *C. albicans* (Villar, et al. (2005) *Infect. Immun.* 73:4588-4595) and that antifungal defenses are stimulated through a TLR4 signaling mechanism (Weindl, et al. (2007) *J. Clin. Invest.* 117:3664-3672). Studies with human larynx epithelioid carcinoma (HEp-2) cells that were treated with *C. albicans* or *C. albicans* metabolites revealed changes in the actin cytoskeleton, reduced membrane ruffling and decreased cell motility (Tsarfaty, et al. (2000) *FEMS Microbiol. Lett.* 189:225-232; Sandovsky-Losica, et al. (2002) *FEMS Microbiol. Lett.* 215:57-62). *C. albicans* has also been shown to cause a reorganization of the cytoskeleton in neutrophils and macrophages (Kolotila & Diamond (1988) *Infect. Immun.* 56:2016-2022; Schindler & Segal (2008) *Med. Mycol.* 46:251-258; Wozniok, et al. (2008) *Cell Microbiol.* 10:807-820) and to elicit the formation of an actin mantle around hyphae (Park, et al. (2005) supra). However, the role(s) of keratinocyte differentiation in candidiasis have not been considered.

SUMMARY OF THE INVENTION

The present invention features a method for identifying an agent that inhibits *Candida albicans*-mediated host cell differentiation. The method involves contacting an undifferentiated keratinocyte with a test agent in the presence of *C. albicans* and determining whether said test agent inhibits differentiation of said keratinocyte thereby identifying an agent that inhibits *Candida albicans*-mediated host cell differentiation. In certain embodiments, the method embraces determining whether the agent increases the expression or activity of calprotectin, increases the expression or activity of an early differentiation marker, decreases the expression or activity of a late differentiation marker, and/or inhibits morphological changes of the keratinocyte.

DETAILED DESCRIPTION OF THE INVENTION

It has now been found that *C. albicans* affects the expression of molecular markers of differentiation. Specifically, it has been demonstrated that *C. albicans* induces behavior similar to the movement-based mechanism leading to cell-cell adhesions of epidermal keratinocytes (Vasioukhin, et al. (2000) *Cell* 100:209-219). The keratinocyte response also includes the expression of the late differentiation markers keratin 13 and SPRR3 and loss of calprotectin. The keratinocyte response is not simply a general response to the presence of a foreign organism, as it does not occur in the presence of the non-pathogenic yeast *Saccharomyces cerevisiae*. The secreted aspartyl proteases (Saps) 4-6, which show increased expression during hyphal growth (White & Agabian (1995) *J. Bacteriol.* 177(18):5215-21; Hube (1996) *Curr. Top. Med. Mycol.* 7:55-69), are strongly implicated in eliciting the keratinocyte response based on the analysis of a sap4-6Δ/sap4-6Δ mutant. The studies presented here are the first to show the potential for *C. albicans* to manipulate oral stratified epithelial cells to a state of differentiation that is favorable for its growth and survival, which is likely to play an important role in the pathogenesis of candidiasis.

Accordingly, the present invention embraces a method for identifying an agent that inhibits *C. albicans*-mediated host cell differentiation by contacting an undifferentiated keratinocyte with a test agent in the presence of *C. albicans* and determining whether the test agent inhibits differentiation of the keratinocyte. Because increased differentiation and hyperkeratinization is a hallmark of oral candidiaisis, inhibition of keratinocyte differentiation or the production and/or secretion of those factors of *C. albicans* that induce keratinocyte differentiation is useful in the prevention or treatment of candidiaisis.

According to the analysis disclosed herein, "*C. albicans*-mediated host cell differentiation" is the modulation of differentiation markers, actin cytoskeleton, and cell motility responses of undifferentiated keratinocytes to factors produced by viable (i.e., living) *C. albicans* cells. Changes in cell differentiation marker expression that are mediated by *C. albicans* include an increase in the expression of late differentiation markers keratin 13 and SPRR3, and a loss or decrease in the expression of calprotectin and early differentiation markers keratin 19 and involucrin, as compared to cells not having been contacted with *C. albicans*.

In this respect, an undifferentiated keratinocyte of the invention is a keratinocyte that constitutively expresses calprotectin and/or other established early differentiation markers of keratinocytes including Keratin 19 and involucrin. In the gingiva and other squamous epithelia, calprotectin localizes to the spinous and subcorneal layers of the stratum spinosum, but it is not seen in the basal or cornified cell layers (Eversole, et al. (1992) *Arch. Oral Biol.* 37:963-968). In so far as monolayer keratinocyte cultures do not cornify under standard culture conditions, these cells can be held in an undifferentiated state and express markers such as calprotectin, Keratin 19 and involucrin in cell culture. Accordingly, exemplary undifferentiated keratinocytes of use in the present invention include immortalized gingival or vaginal keratinocyte cell lines and primary keratinocytes derived from oral or vaginal epithelial mucosa (Ross & Herzberg (2001) *Infect. Immun.* 69:3248-3254; Venkataraman, et al. (2005) *J. Immunol.* 175: 7560-7567). In particular embodiments, an undifferentiated keratinocyte of the invention is characterized as being non-keratinized or lacking keratinization.

The cells of the screening method of the invention can be cultured as exemplified herein or under other suitable conditions of temperature, incubation time, optical density, plating density and media composition corresponding to the nutritional and physiological requirements of the cells. While the present invention particularly embraces a cell-based assay using isolated undifferentiated keratinocytes, it is contemplated that the present assay could be adapted to an in vivo screen, e.g., using an animal model of candidiasis.

The screening method of the present invention can be carried out using any suitable assay format, e.g., multi-well plates, arrays of cells on plates, and the like, that allows rapid preparation and processing of multiple reactions. Stock solutions of the agents as well as assay components are prepared manually and all subsequent pipetting, diluting, mixing, washing, incubating, sample readout and data collecting is done using commercially available robotic pipetting equipment, automated work stations, and analytical instruments for detecting the output of the assay.

In addition to the reagents provided above, a variety of other reagents can be included in the screening assays of the invention. These include reagents like salts, neutral proteins, e.g., albumin, detergents, etc. Also, reagents that otherwise improve the efficiency of the assay, such as protease inhibitors, nuclease inhibitors, and the like can be used.

Test agents which can be screened in accordance with the methods of the present invention are generally derived from libraries of agents or compounds. Such libraries can contain either collections of pure agents or collections of agent mixtures. Examples of pure agents include, but are not limited to, proteins, antibodies, aptamers, peptides, proteinase inhibitors, nucleic acids, oligonucleotides, IRNA, carbohydrates, lipids, synthetic or semi-synthetic small organic molecules, and purified natural products. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active agent from the mixture for characterization and development as a therapeutic drug. In particular, the mixture so identified can be sequentially fractionated by methods commonly known to those skilled in the art which can include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

As indicated, the screening method involves contacting an undifferentiated keratinocyte with a test agent in the presence of *C. albicans* and determining whether the agent inhibits differentiation of the keratinocyte. The step of determining whether differentiation has been inhibited can be carried out using one or more methods. For example, in so far as *C. albicans* has been shown to decrease expression of calprotectin and early differentiation markers, it can be determined whether the agent increases or enhances (e.g., by 10%, 20%, 30%, 40%, 50%, 60%, 70%, 80%, 90%, or 95%) the expression or activity of calprotectin or other early differentiation markers of keratinocytes (e.g., keratin 19 and involucrin) in the test cell as compared with a control keratinocyte which has not been contacted with the test agent. Alternatively, or in addition to, it can be determined whether the test agent decreases or reduces (e.g., by 10%, 20%, 30%, 40%, 50%, 60%, 70%, 80%, 90%, or 95%) the expression or activity of late differentiation markers (e.g., SPRR3 and keratin 13) in the test cell as compared to a control keratinocyte which has not been contacted with the test agent. One of skill in the art will appreciate that any well-established method can be employed for determining whether the agent modulates the expression or activity of the markers disclosed herein. For example, standard northern blot, dot blot, microarray or RT-PCR analyses can be used to monitor mRNA levels. Optionally, protein levels can be determined by western blot analysis or measuring activity (e.g., fluorescence) of a reporter protein (e.g., luciferase or GFP) fused to the promoter of the marker (i.e., a reporter protein assay). Alternatively, or in addition to, it can be determined whether the test agent inhibits the morphological changes associated with *C. albicans*-mediated differentiation, e.g., increased motility, reorganization of the actin cytoskeleton, decrease in average keratinocyte cell area, and/or loss of adherin junctions as described herein, when compared to a control cell not in the presence of the test agent.

In some embodiments of the invention, agents identified in the screening assay will target keratinocytes by, e.g., modulating gene expression and/or morphological changes which are mediated by contact with *C. albicans*. In other embodiments, agents identified in the screening assay will target secreted products of *C. albicans* (e.g., aspartyl proteinases), which mediate keratinocye differentiation. Accordingly, agents that inhibit *C. albicans*-mediated keratinocyte differentiation will be useful in various applications including inhibiting the differentiation of keratinocytes, inhibiting changes in keratinocyte gene expression mediated by *C. albicans* (e.g., loss of calprotectin expression), inhibiting the loss of keratinocyte adherens junctions in the presence of *C. albicans*, protecting barrier integrity, inhibiting the interaction between keratinocytes and aspartyl proteinases secreted by *C. albicans*, and for use as research tools in the study of keratinocyte-*C. albicans* interactions. Methods for analyzing these responses are well-known in the art and disclosed herein.

In addition to the identification of therapeutic agents, the instant assay system can be further used to gain a better understanding of the contribution of individual factors such as hyphae formation, Saps and phospholipases during the invasion of *C. albicans* at distinct human tissues. The instant cell-based assay is advantageous over other non-vertebrate model systems because it offers precise control of host and environment and provides great potential for genetic studies such as the generation and usage of knockout models. Understanding the molecular mechanisms of interaction between *C. albicans* and the host epithelium is important for designing new strategies to prevent spread of the organism that may lead to severe mucosal disease and increase the risk of systemic disease in compromised hosts. In vitro systems using epithelial cells that function in formation of the epithelial barrier to study *C. albicans* mutants are useful tools for deciphering host pathogen cross-talk that takes place on the wet mucosal surfaces of human hosts.

In so far as agents identified in the screening assay of the invention ultimately inhibit *C. albicans*-mediated keratinocyte differentiation, which contributes to *C. albicans* infectivity and pathogenesis, the present invention also relates to methods for preventing and/or treating candidiasis in a subject using agents of the invention. Such methods involve administering to a subject in need of treatment an effective amount of an agent identified herein thereby inhibiting *C. albicans*-mediated keratinocyte differentiation and preventing and/or treating candidiasis in the subject. In most cases the subject being treated will be a human being, but treatment of agricultural animals, e.g., livestock and poultry, and companion animals, e.g., dogs, cats and horses, is also contemplated. The dosage or effective amount of an agent is an amount which achieves the desired outcome of preventing or reducing at least one sign or symptom of candidiasis.

To evaluate the efficacy of agents of the invention, one of skill will appreciate that a model system of candidiasis can be utilized to evaluate the adsorption, distribution, metabolism and excretion of a compound as well as its potential toxicity in acute, sub-chronic and chronic studies.

For therapeutic use, it is generally desirable that the agents of the present invention be provided to a subject in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions appropriately formulated for parenteral (for example, by intravenous, intraperitoneal, subcutaneous or intramuscular injection), topical (including buccal and sublingual), oral, intranasal, intravaginal, or rectal administration can be prepared according to standard methods. In particular embodiments, the agents of the invention would be administered in oral gel formulations such as those described in Aksungur, et al. ((2004) J. Control Release 98:269-79) or Buchsel (2008) Expert Opin. Drug Metab. Toxicol. 11:1449-54), wherein bioadhesive and antimicrobial properties offer the palliative effects of an occlusive dressing and the potential for delivering drugs, including anti-candidal agents.

The selected dosage level will depend upon a variety of factors including the activity of the particular agent or molecule employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of an agent at levels lower than that required in order to achieve the desired therapeutic effect and gradually increase the dosage until the desired effect is achieved.

The invention is described in greater detail by the following non-limiting examples.

Example 1

Materials and Methods

Strains and Growth Conditions. *C. albicans* strains used in this study are listed in Table 1. The strains were maintained on YNB plates and freshly prepared every week. The liquid culture was grown in YNB medium (1.7 grams YNB without amino acids and ammonium sulfate (Fisher Scientific, Pittsburgh, Pa.); 5 grams ammonium sulfate; 9 grams glucose and 10 ml of 0.02% Biotin (Sigma-Aldrich, St. Louis, Mo.) per liter). The *S. cerevisiae* strain was maintained on YPD plates and the liquid culture was grown in YPD medium containing 10 grams Yeast extract, 20 grams Peptone (BD Bioscience, San Jose, Calif.) and 10 grams dextrose (Fisher Scientific, Pittsburgh, Pa.). Cultures were grown in 10 ml YNB or YPD in a rotary shaker at 250 r.p.m. at 30° C. overnight for use in incubation experiments.

TABLE 1

| Strain | Genotype | Source |
| --- | --- | --- |
| UnoPP-1 | ura3Δ::imm434/ura3Δ::imm434 eno1Δ::URA3/ENO1 | Postlethwait & Sundstrom (1995) *J. Bacteriol.* 177: 1772-1779 |
| CAC1-1A1E1 | as UnoPP-1, but cap1::hisG/cap1::hisG | Bahn & Sundstrom (2001) *J. Bacteriol.* 183: 3211-3223 |
| CAH7-1A1E2 | as UnoPP-1, but hwp1::hisG/hwp1::hisG | Sundstrom, et al. (2002b) *Infect. Immun.* 70: 3281-3283 |
| HLC52 | ura3Δ::imm434/ura3Δ::imm434 efg1ΔhisG/efg1ΔhisG-URA3-hisG | Lo, et al. (1997) *Cell* 90: 939-949 |
| 1843 | ura3Δ::imm434/ura3Δ::imm434 als3laΔ/als3saΔ-URA3 | Zhao, et al. (2004) *Microbiology* 150: 2415-2428 |
| DSY459 | Δsap6::hisG/Δsap6::hisG Δsap4::hisG/Δsap4::hisG Δsap5::hisG/Δsap5::hisG-URA3-hisG | Sanglard, et al. (1997) *Infect. Immun.* 65: 3539-3546 |
| FY86 *S. cerevisiae* | MATα his3Δ200 leu2Δ1 ura3-52 | Winston, et al. (1995) *Yeast* 11: 53-55 |

Antibodies.

The following antibodies were used: mouse monoclonal anti-keratin 13 and anti-α-tubulin (Clone B512) both from Sigma-Aldrich, St Louis, Mo., anti-involucrin (US Biological, San Antonio, Tex.), anti-calprotectin AB-1 (Laboratory Vision, Fremont, Calif.) and rabbit polyclonal antibodies directed against E-cadherin (Santa Cruz Biotechnology, Santa Cruz, Calif.), SPRR3 (Alexis, San Diego, Calif.) and keratin 19 (Abcam, Cambridge, Mass.). Secondary antibodies included goat anti-mouse IgG and goat anti-rabbit IgG labeled with ALEXA Fluor 488 or 594 (Molecular Probes, Eugene, Oreg.), and goat anti-mouse IgG and goat anti-rabbit IgG labeled with horseradish peroxidase (Southern Biotech, Birmingham, Ala.).

Cell Culture and Immunostaining.

The oral mucosal cell line, OKF6/TERT-2 keratinocytes (Dickson, et al. (2000) *Mol. Cell. Biol.* 20:1436-1447), was initiated and expanded in keratinocyte serum-free medium (K-SFM) (Invitrogen, Carlsbad, Calif.) at 37° C. in a 5% $CO_2$ in air atmosphere. Cells were grown in 10-cm dishes and were fed every other day with 10 ml of K-SFM medium. Prior to co-culture with wild-type *C. albicans*, OKF6/TERT-2 cells that were grown in low-calcium conditions to ~30% confluence resemble keratinocytes in the intermediate layers of the stratified squamous epithelium that do not express late differentiation markers. OKF6/TERT-2 keratinocytes were split when they reached 20-30% confluence ($7-9 \times 10^5$ cells) followed by a 1:3 dilution. Before incubation, OKF6/TERT-2 keratinocytes were grown on coverslips and fresh medium was applied prior to adding fungi.

For cocultures of keratinocytes with fungi, an overnight culture of *C. albicans* or *S. cerevisiae* was grown at 30° C., pelleted and resuspended in PBS. $8.5 \times 10^6$ cells were added to one 10-cm dish at a final concentration of $8.5 \times 10^5$ $ml^{-1}$. Dishes were then incubated for 3, 6, 12 and 24 hours at 37° C. in a 5% $CO_2$ in air atmosphere. The number of cell-associated *C. albicans* organisms was counted from randomly selected microscopic fields after OKF6/TERT-2 cells were stained with 0.5 mM rho/pha and *C. albicans* was visualized with calcofluor white. *C. albicans* was classified as cell-associated when the presence of an actin-mantle surrounding fungi was detected by fluorescence microscopy (Filler, et al. (1995) *Infect. Immun.* 63:976-983).

Heat-killed *C. albicans* cells were prepared from overnight cultures of wild-type *C. albicans* grown at 30° C. in YNB- or K-SFM followed by treatment at 65° C. for 1 hour. Heat-killed fungi were pelleted, resuspended in K-SFM and added to cultures of OKF6/TERT-2 keratinocytes followed by incubation for 24 hours as described above.

To investigate the role of secreted virulence factors, wild-type *C. albicans* was cocultured with OKF6/TERT-2 cells in K-FSM medium at 37° C. for 24 hours as described above. The medium was removed from cell culture dishes and clarified in a clinical centrifuge. The status of the clarified supernatant was determined by microscopy and then added to cultures of human oral keratinocytes for 24 hours, followed by immunostaining and microscopy.

For immunostaining, cells were fixed with 4% paraformaldehyde in 4% sucrose containing PBS for 20 minutes, quenched with 50 mM ammonium chloride for 10 minutes followed by permeabilization with 0.2% TRITON X-100 for 5 minutes. Cells were washed with 0.2% gelatin in PBS and incubated successively with primary (1:100) and secondary antibodies (1:300) for 1 hour each, with several washes after each antibody incubation. F-actin was detected in fixed and permeabilized cells with 0.5 μM rhodamine/phalloidin (rho/pha) (Sigma-Aldrich, St Louis, Mo.). Coverslips were mounted on glass slides with DABCO (Sigma-Aldrich) and observed by fluorescence microscopy.

Immunofluorescence Microscopy and Live Cell Imaging.

Fixed samples were analyzed by fluorescence deconvolution microscopy using a ZEISS AXIOPLAN2 microscope (Carl Zeiss, Thornwood, N.Y.) equipped with a Hamamatsu Orca II C4742-98 camera and the Mercury arc lamp HBO100 as a light source with Atto Arc II (Omega Optical, VT), and filter sets for FITC, TRITC and DAPI fluorescence. Metamorph imaging software (Universal Imaging, PA) was used to control illumination shutters, camera exposure and image acquisition.

For live cell imaging, OKF6/TERT-2 keratinocytes were grown on 12-mm glass coverslips and removed from 10-cm dishes after incubation with *C. albicans* or *S. cerevisiae* and placed onto microscope chambers (Blocker, et al. (1996) *J. Biol. Chem.* 271:3803-3811). Chambers were filled with K-SFM medium to maintain the cells and sealed with VALAP (a 1:1:1 heated mixture of VASELINE, lanolin and paraffin). Cells were imaged over periods of 10 minutes at room temperature (25-30° C.). Cell motility and cellular edge activity were determined by VEC-DIC microscopy (Allen, et al. (1981) *Cell Motil. Cytoskeleton* 1:291-302; Weiss, et al. (1999) Video microscopy. In *Electronic Light Microscopy in Biology—a Practical Approach.* Lacey, A. J. (ed.). Oxford: IRL Press, pp. 221-278) using a 1.4 NA oil immersion condenser, a 63×/1.4 NA Plan APOCHROMAT oil DIC objective or a 100×/1.4 NA Plan APOCHROMAT oil DIC objective, and a mercury arc lamp (HBO 100). DIC images were taken in real time with a Hamamatsu video C2400 camera (Hamamatsu Photonics). The digital processing of the DIC signal was performed using an ARGUS-20 real-time image processor (Hamamatsu Photonics) and processed images were recorded directly onto a SONY SVO-9500MD S-VHS video recorder. Microscope control and image acquisition were done using Metamorph imaging software (Universal Imaging, PA).

Line Scan Analysis and Quantification of Cell Motility.

To analyze immunofluorescence data, line scan analysis and measurements of fluorescence intensity were performed (Komarova, et al. (2005) *Mol. Biol. Cell* 16:5334-5345) using the Metamorph software. Analysis of intensity profiles along 1-pixel-wide regions through single cells or along 200-pixel-wide regions at cell-cell adhesions was performed in Metamorph after subtracting external background.

Protrusion velocity of the leading edge was analyzed from time-lapse series of images acquired at one frame per second. Kymographs were then generated from time-lapse series at the margins of individual cells (Hinz, et al. (1999) *Exp. Cell Res.* 251:234-243) with the Metamorph software. Cell sizes were determined from threshold images of single cells or cells with defined cell edges using the trace region tool of Metamorph. EXCEL (MICROSOFT) was used to generate bar graphs of cell size, protrusion velocities and fluorescence intensities. Statistical significance of data obtained from measurements of cell sizes and protrusion velocities was determined by the two-tailed Student's t-test.

Western Blot Analysis.

OKF6/TERT-2 keratinocytes were incubated with *C. albicans* strains or *S. cerevisiae* as described above and lysed in 400 μl sample buffer (2×). Equal amounts of protein were separated on 10% SDS-PAGE gels and transferred to a PVDF membrane (Millipore, Billerica, Mass.). Membranes were blocked with 5% milk in TBS-TWEEN for 20 minutes, and then probed for 1 hour with primary antibodies against E-cadherin and tubulin diluted in blocking solution as indicated. Membranes were exposed for 1 hour to the appropriate horseradish peroxidase-conjugated secondary antibodies diluted 1:10000 in blocking solution. Bound antibodies were detected using ECL (Amersham, Piscataway, N.J.).

Histology.

Tissues were fixed in 10% buffered formalin, embedded in paraffin, sectioned (5-μm), stained with the PASH stain, which included periodic acid-Schiff reagent to visualize fungi followed by counterstaining with haematoxylin for characterization of host cells. Stained tissue was viewed using an OLYMPUS BX 60 microscope and photographed using an OPTRONICS MACROFIRE camera Model S99831.

Example 2

Development of a Keratinocyte Cell Culture System

The oral keratinocyte cell line OKF6/TERT-2 was used to investigate whether keratinocyte differentiation programs are influenced by the presence of *C. albicans*. When grown at low confluency (30%) in the absence of inducers of differentiation, OKF6/TERT-2 cells resemble keratinocytes in the intermediate layers of the stratified squamous epithelium; the late differentiation markers SPRR3 and keratin 13 (Kartasova, et al. (1988) *Mol. Cell. Biol.* 8:2204-2210; Jetten, et al. (1989) *Exp. Cell Res.* 182:622-634; Hohl, et al. (1995) *J. Invest. Dermatol.* 104:902-909) are not produced.

Example 3

*C. albicans*-Mediated Cytoskeletal Alterations and Cell Motility of Human Oral Keratinocytes

*C. albicans* yeast forms were added to cultures of human oral keratinocytes at a yeast:keratinocyte ratio of about 0.3:1.0. By 6 hours, approximately 14% (n=428 cells) of keratinocytes were associated with *C. albicans* hyphae. A prominent actin mantle was observed around the cell-associated hyphae, as has been seen using endothelial cells and non-differentiating epithelial and epithelioid cancerous cell lines (Filler, et al. (1995) supra; Tsarfaty, et al. (2000) supra; Park, et al. (2005) supra; Phan, et al. (2007) supra).

Human oral keratinocytes responded to the presence of *C. albicans* by a dramatic reorganization of the actin cytoskeleton that was accompanied by increased motility. Despite the fact that only a small fraction of the keratinocytes was associated with hyphae, actin reorganization and motility, as well as alterations in the expression of differentiation markers and calprotectin, were uniformly observed throughout the culture. Alterations in the actin cytoskeleton in the presence of *C. albicans* have been observed for nondifferentiated cell lines in other studies (Filler, et al. (1995) supra; Tsarfaty, et al. (2000) supra); however, the extent of cytoskeletal reorganization and the relationship to cellular motility were not described.

To investigate the detailed dynamic changes in the actin cytoskeleton and to quantify changes in motility of human oral keratinocytes in the presence of *C. albicans*-forming hyphae, specific fluorescence markers and video-enhanced contrast differential interference contrast (VEC-DIC) microscopy were used. Prior to the addition of *C. albicans*, most human oral keratinocytes exhibited a round profile with an average cell area of 415 μm$^2$. F-actin was found primarily at the cell periphery and within long filopodial projections. These features of keratinocytes at 0 hour were retained in control cultures in the absence of *C. albicans* over the 24-hour time period of study. Incubation in the presence of *C. albicans* for 3 hours led to a 2.4-fold increase in the average keratinocyte cell area. Stress fibers were the most prominent actin filament structures, although a few lamellipodial protrusions were observed. After 6 hours of incubation, the cell area had reached a maximum (1417±408 μm$^2$). Stress fibers disappeared and extensive lamellipodia had formed with a dense F-actin network at the leading edge. After 12 hours of incubation, the cell area decreased by 1.8 times compared with the 6-hour time interval and the actin filament structures became less distinct. As the cells began to round up, actin retraction fibers accumulated at the cell edges as the cells became detached from the culture dish. After 24 hours of incubation, the cell area had decreased and was found to be about 1.5 times smaller than for human oral keratinocytes cultured without C. albicans. Actin retraction fibers and actin filament tangles were observed at the cell periphery.

To determine the relationship of actin filament structures observed by fluorescence microscopy to cell motility, the behavior of the leading edges of human oral keratinocytes was examined by VEC-DIC microscopy. The protrusive activity of the leading edges of individual cells was recorded in real-time and displayed as kymographs (Hinz, et al. (1999) supra).

Prior to the addition of C. albicans, human oral keratinocytes at 0 hour demonstrated cycles of filopodial protrusion and retraction with an average protrusion velocity of $1.56\pm0.6$ µm $min^{-1}$. At the early time intervals (3-6 hours), the protrusion/retraction cycle of lamellipodia differed from that of untreated human oral keratinocytes. Kymographic analysis showed that cells exhibited repeated protrusions with little retraction after 3 hours of incubation. However, the protrusion velocity was not significantly different ($1.74\pm0.66$ µm $min^{-1}$) compared with untreated human oral keratinocytes ($P>0.2$). After 6 hours of incubation, the lamellipodia showed a high degree of protrusive activity and the velocity was 80% higher ($2.82\pm1.2$ µm $min^{-1}$) than in untreated human oral keratinocytes ($P<0.0001$). At longer time intervals (12-24 hours) the protrusive activity was strongly reduced and the velocity had decreased by 68% in comparison with the 6-hour time interval ($0.9\pm0.48$ µm $min^{-1}$). No protrusive activity was detected in human oral keratinocytes after incubation with C. albicans for 24 hours.

In summary, C. albicans activated the actin cytoskeleton to form stress fibers followed by lamellipodia, and increased cell motility during the early time intervals (3-6 hours) of incubation (Tsarfaty, et al. (2000) supra). At the longer time intervals (12-24 hours) of incubation, actin filament remodeling and cell motility decreased. The effects of C. albicans through the 6-hour time interval are reminiscent of a movement-based mechanism leading to cell-cell adhesions of epidermal keratinocytes (Vasioukhin, et al. (2000) Cell 100:209-219), whereas the rounding of keratinocytes and release from the substratum in the latter time points resemble gingival keratinocytes in the presence of the pathogen Porphyromonas gingivalis (Belton, et al. (1999) Cell Microbiol. 1:215-223; Nisapakultorn, et al. (2001) Infect. Immun. 69:4242-4247).

Example 4

C. albicans-Mediated Formation and Dissolution of Cell-Cell Adhesions

To further investigate the possibility that the changes in the actin cytoskeleton, cell size and protrusion velocities described herein could be related to the movement-based mechanism for the formation of cell-cell adhesions (Vasioukhin, et al. (2000) supra), the cells were evaluated over time for the presence of E-cadherin an adhesion molecule, which serves as a marker of adherens junctions between connecting keratinocytes (Vasioukhin, et al. (2000) supra; Gumbiner (2005) Nat. Rev. Mol. Cell. Biol. 6:622-634).

In the absence of C. albicans, human oral keratinocytes exhibited a diffuse E-cadherin staining pattern by immunofluorescence, with a low concentration at cell-cell contacts, indicating an absence of cell-cell adhesions. Coculture with C. albicans initially led to an increase in cell-cell contacts between keratinocytes followed by the formation of keratinocyte cell-cell adhesions. After 3 hours of incubation, new intercellular contacts formed that were accompanied by the presence of actin stress fibers and E-cadherin puncta. After 6 hours of incubation, the number of E-cadherin-labeled puncta at cell-cell adhesions increased several fold and the puncta of adjacent cells were partially aligned in formations resembling cell-cell adhesions. Line scans at cell-cell contacts showed peak fluorescence intensities for F-actin and E-cadherin at 3 and 6 hour time intervals, indicating that cell-cell adhesions had formed. After 12 hours of incubation, the cell-cell adhesions began to disintegrate as indicated by gaps between cells and a reduction in E-cadherin staining. But some of the E-cadherin labeled puncta remained localized to the membrane edges of interconnecting actin retraction fibers. Cell-cell adhesions were disrupted completely and cells were separated from each other after 24 hours of incubation. No staining was observed with the anti-E-cadherin antibody at this time interval.

The expression of E-cadherin in human oral keratinocytes during incubation with C. albicans was determined by western blot analysis of cell lysates. The E-cadherin level decreased in a time-dependent manner during the incubation of with C. albicans. Even though cell-cell adhesions were present at 3 and 6 hours, the amount of E-cadherin was decreasing over this period and was nearly undetectable by 24 hours. Together, these findings indicate that the formation and disruption of cell-cell adhesions of human oral keratinocytes are caused by incubation with C. albicans.

Example 5

Expression of Late Differentiation Markers

The formation of cell-cell adhesions indicated that human oral keratinocytes might respond to the presence of C. albicans by entering a differentiation program (Vaezi, et al. (2002) Dev. Cell 3:367-381). Keratinocytes cultured in low-calcium conditions (low calcium, 0.3 mM in K-SFM) prior to the addition of C. albicans appeared to be in the process of transitioning between the undifferentiated and early differentiated states. Keratin 19, a marker of undifferentiated keratinocytes (Larouche, et al. (2005) Methods Mol. Biol. 289:103-110), and involucrin that is expressed in cells at an early stage of differentiation (Cai, et al. (2006) Pflugers Arch. 452:43-52), were very prominent in the perinuclear region of the cell, whereas levels of the late differentiation markers, SPRR3 and keratin 13, were low as expected for keratinocytes in the early stages of differentiation. The expression of differentiation markers did not change over the 24-hour incubation period in the absence of fungi.

In the presence of C. albicans the expression levels of keratin 19 and involucrin began to decrease at 3 hours and continued to decrease at 6 hours. At the later time intervals (12-24 hours), the expression levels decreased further. Fluorescence intensity measurements showed that human oral keratinocytes incubated with C. albicans had more than a three-fold decrease in keratin 19 and a 2.6-fold decrease in involucrin at 24 hours relative to untreated cells.

In contrast, the expression levels of the late differentiation markers keratin 13 and SPRR3 increased at 3 hours as revealed by the image brightness and fluorescence intensity measurements. At 6 hours of incubation, the expression levels of keratin 13 and SPRR3 exhibited 2.5-fold and nine-fold increases, respectively, compared with untreated cells. Furthermore, immunolocalization revealed filamentous staining of keratin 13 within human oral keratinocytes. At the late time intervals (12-24 hours), the fluorescence intensities of keratin 13 and SPRR3 increased further, and both markers exhibited the highest expression levels at 24 hours.

Example 6

Reduced Expression of the Antimicrobial Protein Calprotectin

To address whether the induction of differentiation by *C. albicans* could affect the antimicrobial activity of human oral keratinocytes, immunostaining for calprotectin, an anionic, calcium-binding protein complex that is expressed in oral keratinocytes (Wilkinson, et al. (1988) *J. Cell Sci.* 91:221-230; Eversole, et al. (1992) supra), was performed. Calprotectin has been demonstrated to reduce growth of bacteria and fungi (Steinbakk, et al. (1990) *Lancet* 336:763-765; Sohnle, et al. (1996) *J. Infect. Dis.* 174:1369-1372) and is expressed in the spinous layer but not in the superficial layers of the oral epithelium (Eversole, et al. (1997) *Oral Surg. Oral Med. Oral Pathol. Oral Radiol. Endod.* 84:372-380).

Calprotectin was highly expressed in untreated human oral keratinocytes, indicating that its expression does not depend on the presence of a pathogen in cultured cells. The expression level of calprotectin gradually decreased over time in the presence of wild-type *C. albicans* when SPRR3 and keratin 13 increased, thereby coupling the loss of antifungal activity with terminal differentiation.

Example 7

Minimal Alterations by the Non-Pathogenic Yeast, *S. cerevisiae*

In contrast to the dramatic keratinocyte response that occurred in the presence of *C. albicans*, cultures incubated for 24 hours with the non-pathogenic yeast, *S. cerevisiae*, did not alter actin filament dynamics or cell motility compared with keratinocytes alone and caused only a minor change in cell area. Other minor changes in keratinocytes in the presence of *S. cerevisiae* included a slight decrease in keratin 19, and a slight increase in keratin 13 compared with human oral keratinocytes without added fungi. Culturing keratinocytes with *S. cerevisiae* did not lead to a loss of E-cadherin or an increase in SPRR3. The major changes seen in human oral keratinocytes were not induced by environmental yeast.

Example 8

Effects of *C. albicans* Mutants With Reduced Abilities to Form True Hyphae

To investigate the properties of *C. albicans* that are required to induce cellular responses in human oral keratinocytes, the *C. albicans* mutants efg1Δ/efg1Δ, cap1Δ/cap1Δ, hwp1Δ/hwp1Δ, als3Δ/als3Δ and sap4-6Δ/sap4-6Δ (Lo, et al. (1997) supra; Sanglard, et al. (1997) supra; Bahn & Sundstrom (2001); Sundstrom, et al. (2002) supra; Zhao, et al. (2004) supra) were analyzed in cocultures with human oral keratinocytes. For the experiments using mutants, a single incubation period of 24 hours was selected because it represented the time interval at which the responses of human oral keratinocytes to the mutants were most easily distinguished from each other and from the wild-type strain.

As the ability to form hyphae has been shown to be critical for the virulence of *C. albicans*, it was determined whether the efg1Δ/efg1Δ mutant that exhibited growth restricted to the yeast form and the cap1Δ/cap1Δ mutant that grew predominantly in the pseudohyphal form (Sudbery, et al. (2004) *Trends Microbiol.* 12:317-324) differed from wild-type in the ability to induce cytoskeletal changes and expression of differentiation markers in human oral keratinocytes. The efg1Δ/efg1Δ mutant is missing a gene that encodes a transcription factor that is required for activation of hypha-specific genes. The cap1Δ/cap1Δ mutant is missing a gene that encodes the adenylate cyclase-associated protein, which results in reduced cAMP levels during germ tube induction, a delay in germ tube induction and reduced expression of hypha-specific genes.

The efg1Δ/efg1Δ and cap1Δ/cap1Δ mutants were able to induce actin cytoskeletal alterations but with retarded kinetics; after 24 hours of incubation with the efg1Δ/efg1Δmutant or the cap1Δ/cap1Δ mutant, keratinocyte responses appeared similar to those that were incubated for only 6 or hours, respectively, with wild-type *C. albicans*. Even though the effects of the efg1Δ/efg1Δ mutant for 24 hours were mild, they were much more pronounced than the effects caused by the non-pathogen *S. cerevisiae*. The efg1Δ/efg1Δmutant caused the formation of lamellipodia and a dense F-actin network at the leading edge similar to the 6 hour cocultures with the wild-type strain, and a high degree of cell expansion ($1413\pm438$ $\mu m^2$; $P<0.0001$). A comparison of cell areas and appearances of actin staining showed that the effects of the cap1Δ/cap1Δ mutant were intermediate between those of the efg1Δ/efg1Δ mutant and those of the wild-type strain. The lamellipodia had disappeared, and actin retraction fibers had formed at the cell edge. Consistent with the ability of the efg1Δ/efg1Δ and cap1Δ/cap1Δ mutants to elicit keratinocyte responses, the lamellipodial and filopodial protrusion velocities of $0.71\pm0.32$ and $0.70\pm0.32$ $\mu m\ min^{-1}$, respectively, were midway between keratinocytes cultured without fungi ($1.56\pm0.6$ $\mu m\ min^{-1}$) and keratinocytes in the presence of the wild-type strain, which no longer exhibited protrusion at the 24-hour time interval.

The retarded kinetics of the human oral keratinocyte response to the efg1Δ/efg1Δ and cap1Δ/cap1Δ mutants described herein were also found in the formation of cell-cell adhesions and the expression of SPRR3, keratin 13 and calprotectin. The cell-cell adhesions in human oral keratinocytes were not disrupted as was the case in the presence of the wild-type strain, but were prominent after hours of coculture with both mutants as indicated by partial colocalization of F-actin and E-cadherin between two interconnecting cells. The presence of E-cadherin in cell lysates as shown by western blot analysis was consistent with the presence of cell-cell adhesions, which contrasted with cultures incubated with the wild-type strain for 24 hours, in which E-cadherin was barely detectable.

The levels of expression of the late differentiation markers SPRR3 and keratin 13 induced by both the efg1Δ/efg1Δ and cap1Δ/cap1Δ mutants were significantly lower than those induced by the wild-type *C. albicans* strain at 24 hours. The cap1Δ/cap1Δ mutant induced more expression of keratin 13 than the efg1Δ/efg1Δ mutant. The efg1Δ/efg1 and cap1Δ/cap1Δ mutants were able to cause wild-type reductions in involucrin although the efg1Δ/efg1Δ mutant showed a diminished ability to reduce the level of keratin 19.

Consistent with the inverse correlation of calprotectin expression compared with SPRR3 and keratin 13, the antimicrobial protein calprotectin was highest in the presence of efg1Δ/efg1Δ mutant, intermediate in the cap1Δ/cap1Δ mutant and lowest in the wild-type. Effects on expression of differentiation markers and calprotectin induced by the three mutants were consistent with the trend that was established in the analysis of cytoskeletal organization, protrusion velocities and cell-cell adhesions; the mutants were able to cause modulation of differentiation marker expression, but to a lesser degree than wild-type *C. albicans*.

These data showed that the degree of reorganization of the actin cytoskeleton and changes in cell motility correlated with the ability of *C. albicans* mutants to form hyphae. The modulation of differentiation markers and calprotectin also correlated with the ability to form hyphae. The results indicate that the presence of hyphal growth forms is required for maximal keratinocyte responses to *C. albicans*.

Example 9

Role of Hypha-Specific Virulence Factors in Eliciting Human Oral Keratinocyte Responses to *C. albicans*

The hwp1Δ/hwp1Δ, als3Δ/als3Δ and sap4-6Δ/sap4-6Δ mutants that are not defective in production of true hyphae but lack virulence factors associated with hyphal growth were analyzed for elicitation of the keratinocyte response. The hwp1Δ/hwp1Δ mutant is missing the gene that codes for Hwp1 and shows reduced adherence to buccal epithelial cells, but forms normal germ tubes in laboratory media and in animal tissue (Staab, et al. (1999) *Science* 283:1535-1538; Sundstrom, et al. (2002) supra). To test the role of the Saps, a mutant with deletions in the genes encoding Saps4-6, sap4-6Δ/sap4-6Δ, was assessed. The reports that Sap5 is highly expressed in patient samples (Naglik, et al. (2008) *Microbiology* 154:3266-3280) and that Sap5p degrades E-cadherin (Villar, et al. (2007) *Infect. Immun.* 75:2126-2135) indicated that Sap5p and possibly other Saps might affect the actin cytoskeleton, cell motility and expression of differentiation markers by human oral keratinocytes.

The effects of the hwp1Δ/hwp1Δ mutant on keratinocytes were only slightly milder than the effects of the wild-type strain. The actin filament tangles most prominent at the cell edge were similar to those seen in the presence of wild-type *C. albicans*. However, the cells treated with the hwp1Δ/hwp1Δ mutant appeared to be less shrunken, the average cell area (438±290 μm$^2$) was slightly larger (P<0.005) and the protrusion velocity was slightly higher (P<0.003), than for cells incubated with the wild-type strain for the same time interval. Cell-cell adhesions in human oral keratinocytes after 24 hours of incubation with the hwp1Δ/hwp1Δ mutant were disrupted and E-cadherin was strongly decreased. E-cadherin was also not detectable in lysates of human oral keratinocytes cultured in the presence of the hwp1Δ/hwp1Δ mutant. The hwp1Δ/hwp1Δ mutant decreased the expression of keratin 19, the early differentiation marker involucrin and calprotectin, although calprotectin was not as reduced as much by the hwp1Δ/hwp1Δ mutant as by the wild-type strain. High levels of SPRR3 and keratin 13 were present at 24 hours in the presence of the hwp1Δ/hwp1Δ mutant in amounts that did not differ significantly from those induced by the wild-type *C. albicans* strain.

The als3Δ/als3Δ mutant, which was not found to be associated with keratinocytes, elicited an intermediate keratinocyte response that appeared more pronounced than that elicited by the mutants that were defective in production of true hyphae. In the presence of the als3Δ/als3Δ mutant, the actin filament tangles most prominent at the cell edge appeared to be as pronounced as those seen in the presence of the hwp1Δ/hwp1Δmutant and wild-type *C. albicans* strains and the cell area was equivalent to that of the hwp1Δ/hwp1Δmutant. The als3Δ/als3Δ mutant modulated the expression of differentiation markers; keratin 19 and involucrin were reduced to levels that were equivalent to those in the presence of the wild-type strain, and the late differentiation marker SPRR3 was increased to a level that was equivalent to that in the presence of the hwp1Δ/hwp1Δ mutant. Keratin 13 was increased in the presence of the als3Δ/als3Δmutant to a level that was equivalent to that induced by the cap1Δ/cap1Δ mutant. The calprotectin level was reduced to a level equivalent to that caused by the hwp1D/hwp1D mutant. The keratinocyte response elicited by the als3Δ/als3Δ mutant was also reduced compared with the wild-type strain in that the protrusion velocity was similar to that caused by the efg1Δ/efg1Δ and cap1Δ/cap1Δ mutants. Furthermore, the retention of E-cadherin-containing cell-cell adhesions and the detection of E-cadherin by western blot analysis after 24 hours in the presence of the als3Δ/als3Δ mutant were similar to the results with the efg1D/efg1D and cap1Δ/cap1Δ mutants.

These results indicate that association of *C. albicans* with keratinocytes is not required to induce actin cytoskeletal changes and modulation of differentiation marker expression by keratinocytes, but does appear to increase the magnitude of the keratinocyte response.

To further investigate the role of secreted factors in eliciting the keratinocyte response, keratinocytes were cultured in the presence of clarified supernatant from media used for growth of hyphae. After 24 hours of incubation, actin retraction fibers had formed and were found at the cellular edges similar to that was observed in the presence of wild-type *C. albicans* hyphae. Immunostaining of differentiation markers revealed reduced expression levels of involucrin and keratin 19 and increased levels of SPRR3 and keratin 13 when compared with cultures of untreated human oral keratinocyte.

The sap4-6Δ/sap4-6Δ mutant was profoundly defective in eliciting the keratinocyte response compared with the other mutants and the wild-type *C. albicans* strain. Consistent with the degradation of E-cadherin by Sap5 (Villar, et al. (2007) supra), the E-cadherin level of keratinocytes in the presence of the sap4-6Δ/sap4-6Δ mutant was as high as in keratinocytes cocultured without fungi. In addition, actin reorganization and the protrusion velocity of keratinocytes cultured in the presence of the sap4-6Δ/sap4-6Δ mutant for 24 hours did not differ from those of keratinocytes cultured without fungi; F-actin was found primarily at the cell periphery and within long filopodial projections, the average cell area (499 μm$^2$) was similar to that of keratinocytes cultured without fungi (415 μm$^2$) and cycles of filopodial protrusion and retraction led to an approximate average protrusion velocity of 1.5 μm min$^{-1}$ that was also similar to cultures in the absence of fungi. Unlike any of the other mutants, the sap4-6Δ/sap4-6Δ mutant was barely able to down-regulate the expression of the early differentiation marker, involucrin and keratin 19, which were reduced by 14% and 32%, respectively, over the 24 hour incubation period. The late differentiation markers were slightly increased in the presence of the sap4-6Δ/sap4-6Δ mutant; the levels of keratin 13 and SPRR3 were increased to 33% and 46%, respectively, compared with cultures in the presence of the wild-type strain. The calprotectin level of keratinocytes in the presence of the sap4-6Δ/sap4-6Δ mutant was only slightly reduced compared with keratinocytes cocultured in the absence of fungi and was almost as high as that found in keratinocytes incubated in the presence of the efg1Δ/efg1Δ mutant for 24 hours. These results showed that the sap4-6Δ/sap4-6Δ mutant elicited the mildest keratinocyte response of all of the mutants, strongly implicating Saps4-6 associated with hyphal growth in the modulation of expression of keratinocyte differentiation markers and calprotectin by *C. albicans*.

To gain information about the effect of mechanical damage to human oral keratinocytes from the presence of inert *C. albicans* cells, heat-killed fungi were prepared from the wild-type strain grown in two different media: YNB, which gives rise to yeast forms, and KSF-medium, which gives rise to mixtures of yeast, pseudohyphal and hyphal growth forms. The heat-killed fungi were not cell-associated with keratinocytes after 24 hours of incubation. Keratinocytes cultured in the presence of heat-killed cells appeared identical to keratinocytes cultured in the absence of fungi, in that F-actin was seen primarily at the cell periphery and within long filopodial projections. In addition, keratinocytes exhibited a diffuse E-cadherin staining pattern as observed by immunofluorescence with a low concentration at cell-cell contacts indicating an absence of cell-cell adhesions. The expression levels of early and late differentiation markers and calprotectin were unchanged compared with keratinocytes cultured in the absence of fungi. These results are consistent with the premise that secreted factors from viable *C. albicans* cells are required to induce the dramatic changes of the actin cytoskeleton, cell motility and modulation of differentiation markers in human oral keratinocytes.

What is claimed is:

1. A method for identifying an agent that inhibits *Candida albicans*-mediated host cell differentiation comprising
   (a) contacting undifferentiated keratinocytes with *C. albicans* for 3 to 6 hours;
   (b) contacting the undifferentiated keratinocytes with a test agent; and
   (c) determining whether said test agent inhibits differentiation of the keratinocytes as measured by:
      (i) an increase in the expression or activity of calprotectin, Keratin 19 or involucrin;
      (ii) a decrease in the expression or activity of Keratin 13 or SPRR3;
      (iii) an increase in motility or reorganization of actin cytoskeleton; or
      (iv) a combination of one or more of (i)-(iii) as compared to control undifferentiated keratinocytes not contacted with the test agent thereby identifying an agent that inhibits *Candida albicans*-mediated host cell differentiation.

2. A method for identifying an agent that inhibits *Candida albicans*-mediated host cell differentiation comprising
   (a) contacting undifferentiated keratinocytes with *C. albicans* for 12 to 24 hours;
   (b) contacting the undifferentiated keratinocytes with a test agent; and
   (c) determining whether said test agent inhibits differentiation of the keratinocytes as measured by:
      (i) an increase in the expression or activity of calprotectin, Keratin 19 or involucrin;
      (ii) a decrease in the expression or activity of Keratin 13 or SPRR3;
      (iii) a decrease in average keratinocyte cell area or loss of adherin junctions; or
      (iv) a combination of one or more of (i)-(iii) as compared to control undifferentiated keratinocytes not contacted with the test agent thereby identifying an agent that inhibits *Candida albicans*-mediated host cell differentiation.

* * * * *